US006882878B2

(12) United States Patent
Schmit et al.

(10) Patent No.: US 6,882,878 B2
(45) Date of Patent: Apr. 19, 2005

(54) RESTRAINING APPARATUS AND METHOD FOR USE IN IMAGING PROCEDURES

(76) Inventors: Berndt P. Schmit, 939 N. Terrace Hills Dr., Salt Lake City, UT (US) 84103; Mark Keeton, 900 Donner Way #205, Salt Lake City, UT (US) 84108; Ben Babusis, 115 S. 1100 East, #706, Salt Lake City, UT (US) 84102

( * ) Notice: Subject to any disclaimer, the term of this patent is extended or adjusted under 35 U.S.C. 154(b) by 0 days.

(21) Appl. No.: 10/736,189

(22) Filed: Dec. 15, 2003

(65) Prior Publication Data

US 2004/0127786 A1 Jul. 1, 2004

Related U.S. Application Data

(63) Continuation of application No. 09/738,423, filed on Dec. 15, 2000, now Pat. No. 6,684,096.

(51) Int. Cl.[7] .................................................. A61B 5/05
(52) U.S. Cl. ........................ 600/415; 600/421; 600/422; 324/318
(58) Field of Search ................................ 600/415, 421, 600/422, 417, 429; 324/318, 307, 320, 321, 322, 309; 128/845

(56) References Cited

U.S. PATENT DOCUMENTS

| | | |
|---|---|---|
| 5,131,412 A | 7/1992 | Rankin |
| 5,143,068 A | 9/1992 | Muennemann et al. |
| 5,195,944 A | 3/1993 | Schlogel |

(Continued)

FOREIGN PATENT DOCUMENTS

WO    WO 9310727 A1    6/1993

OTHER PUBLICATIONS

Karl Dantendorfer et al.; A Study of the Effects of Patient Anxiety, Perceptions and Equipment on Motion Artifacts in Magnetic Resonance Imaging.;*Magnetic Resonance Imaging*, vol. 15, No. 3, Pp. 301–306, 1997. Elsevier Science Inc.
I. S. Francis et al.; The Bead Bag Immobilization Device; *The British Journal of Radiology*, 72 (Sep. 1999), 889–890. London. The British Institute of Radiology.
Keith R. Thulborn et al.; An Integrated Head Immobilization System and High–Performance RF Coil for fMRI of Visual Paradigms at 1.5 T*:Journal of Magnetic Resonance* 139. 26–34 (1999). Academic Press. University of Pittsburgh Medical Center. Pittsburgy, Pennsylvania.

(Continued)

*Primary Examiner*—Thomas Denion
*Assistant Examiner*—Ching Chang
(74) *Attorney, Agent, or Firm*—Parsons Behle & Latimer

(57) ABSTRACT

A restraining apparatus and method for limiting motion on the macro and micro scale during MRI and CT scans, by providing a custom fit, while also improving patient comfort. The restraining apparatus includes a disposable component, including castable and expandable sleeves used to fix the patient into a coil. The castable sleeve encircles the limb of a patient, and is filled with a quickly casting material. The cast material is patient compatible and preferably designed to augment imaging. The resulting cast is MRI compatible, safe and rapid setting, which will decrease the time to set up a patient for scanning, thereby further improving MRI productivity. The expandable sleeve encircles the castable sleeve and is inflatable such that the expandable sleeve conforms to the inner dimensions of a particular MRI coil, CT scanner, or other imaging device. Alternatively, the apparatus includes a castable sleeve for casting around a flex/wrap or surface coil. The surface coil is first cast around the limb of a patient, then the patient is fixed to the magnet.

6 Claims, 8 Drawing Sheets

OTHER PUBLICATIONS

Keith R. Thulborn et al.; An Integrated Head Immobilization System and High–Performance RF Coil for fMRI of Visual Paradigms at 1.5 T:*Journal of Magnetic Resonance*139. 26–34 (1999). Academic Press. University of Pittsburgh Medical Center. Pittsburgy, Pennsylvania.

U.S. PATENT DOCUMENTS

| Patent | Date | Inventor |
|---|---|---|
| 5,305,750 A | 4/1994 | Makita |
| 5,311,882 A | 5/1994 | Gagne |
| 5,361,764 A | 11/1994 | Reynolds et al. |
| 5,379,768 A | 1/1995 | Smalen |
| 5,400,787 A | 3/1995 | Marandos |
| 5,435,302 A | 7/1995 | Lenkinski et al. |
| 5,500,595 A | 3/1996 | Burton |
| 5,560,360 A | 10/1996 | Filler et al. |
| 5,706,813 A | 1/1998 | Filler et al. |
| 5,899,859 A | 5/1999 | Votruba et al. |
| 5,906,205 A | 5/1999 | Hiebert |
| 6,141,580 A | 10/2000 | Hayashi et al. |
| 6,144,203 A | 11/2000 | Richard et al. |
| 6,684,096 B1 * | 1/2004 | Schmit et al. ............... 600/415 |

* cited by examiner

RESTRAINING APPARATUS AND METHOD FOR USE IN IMAGING PROCEDURES

CROSS-REFERENCE TO RELATED APPLICATIONS

This application is a continuation of prior U.S. patent application Ser. No. 09/738,423, filed Dec. 15, 2000 now U.S. Pat. No. 6,684,096 which is hereby incorporated herein by reference.

BACKGROUND

1. The Field of the Invention

The present invention relates generally to apparatus and methods for stabilizing, restraining, and positioning a portion of the body of a patient during a medical procedure. More specifically the present invention relates to apparatus and methods for stabilizing, restraining, and comfortably positioning a portion of the body of a patient, while improving image quality during Magnetic Resonance Imaging and Computerized Tomography scanning procedures.

2. The Background Art

Computerized Tomography ("CT") scanning and Magnetic Resonance Imaging ("MRI") are procedures used for obtaining unique cross sectional views of a patient's internal anatomy, thereby aiding in diagnosis and treatment. CT scanning involves the use of many low dosage x-rays being passed through the body at different angles to produce cross sectional images of body tissue with the aid of a computer. MRI involves the use of electromagnets and short bursts of powerful magnetic fields and radio waves, rather than x-rays, being passed through the body. The bursts stimulate the hydrogen atoms in the patient's tissue to produce a signal that a magnetic coil detects and a computer transforms into an image.

Both of these procedures require a patient's absolute stillness in the area of the body being imaged. Patient motion is an ever-present problem for the radiologist. During the actual sequence the patient must remain absolutely motionless or the images will be blurred, often rendering them uninterpretable. This disruption in the images is known as "motion artifact."

Motion artifact is a constant problem in all MRI because this procedure requires a relatively long period of time to obtain the images. In MRI, the patient must remain motionless for multiple imaging sequences that comprise the total exam. The exam may last 30 to 60 minutes and each sequence typically takes about 4 to 9 minutes to run. While CT scanning has much shorter imaging times than MRI, there are motion considerations in patients who are unable to cooperate. Many head CT scans are performed for the acutely injured patient and for those with sudden mental status changes. Both groups of patients are compromised in their ability to hold still and would benefit from a motion-limiting device.

In either MRI or CT scans, maintaining absolute stillness can be a challenge for an otherwise healthy adult. For an adult afflicted with tremors (such as in Parkinson's Disease), pediatric patients, patients with altered mental status from stroke or trauma, intoxicated patients, and those patients who simply fall asleep during the imaging test and are twitchy sleepers, maintaining stillness may be virtually impossible.

Patient motion can be divided into two categories: macro motion and micro motion. Macro motion occurs on the scale of centimeters and results in the body part of interest actually moving out of the field of view. This results in images that do not include the body part of interest. The patient then has to be "re-scouted" and the sequence repeated once the body part has been re-localized. This results in a loss of about 5 to 7 minutes. Micro motion occurs on a scale of millimeters and may be the result of a patient tremor, cardiac pulsation, breathing, patient restlessness, or patient discomfort resulting in unconscious twitching and shifting. This micro motion results in blurred images, which also have to be repeated. Fortunately, the patient does not need to be re-localized for these repeat sequences.

Radiologists expend extensive effort to combat patient movement. The current practice for combating patient movement involves the use of make-shift restraints from foam pads, pillows, and/or towels. Patients are brought into the MRI machine (or CT scanner) and positioned with their limb or head in the appropriate coil or imaging device. The foam pads, pillows and/or towels are then used with tape and straps to stabilize the body part and obtain a comfortable position. This positioning often takes several minutes and is fraught with poor success. Patient motion occurs because the pads, pillows, etc., do not create a custom fit and are limited in their restraining ability. Likewise, the lack of custom fit cannot create or maintain patient comfort. There are inevitable pressure points that result from a fold in the pillow, the corner or seam of a pad, and/or the edge of the coil or imaging device. The patient may have started the exam feeling quite comfortable, but after 20–30 minutes, an intolerable pressure point develops and the patient is ultimately compelled to shift his body. This even occurs in the normally conscious and cooperative patient despite his best efforts to hold still.

Fundamentally, the foam pad/pillow system is neither comfortable nor does it provide an adequate level of restraint. In addition, foam pads and pillows inherently lack the custom fit or restraint of the limb necessary to avoid all micro and macro motion.

Motion degradation leads to a significant number of non-diagnostic studies and also to considerable waste of resources. MRI time is expensive; rescanning a 5 minute sequence costs about $50 in lost magnet time. If only one sequence is rescanned on every patient on a busy MRI scanner performing 25 exams per day, roughly 125 minutes of imaging time is lost representing about 4 patient slots of at least about $1400 in technical income and roughly $400 in professional income. Clearly, motion can have a significant impact on MRI productivity. Furthermore, the delays related to patient motion will make all the subsequent patients wait, leading to customer dissatisfaction. There are approximately 6000 MR scanners in the United States. Typically, each scanner performs 5–10 brain and/or extremity examinations daily that would benefit from improved restraint and comfort.

While the time penalty for motion on a CT scanner is less severe, many of the studies on acutely head injured patients are impossible to obtain due to motion. There are approximately 6000 CT scanners in the USA. Roughly 5 head CT exams are performed each day per scanner yielding 30,000 studies. Perhaps, half of these are in patients with altered mental state, and therefore high risk of motion. Often times these scans have to be repeated to obtain better images.

BRIEF SUMMARY AND OBJECTS OF THE INVENTION

In view of the foregoing, it is a primary object of the present invention to provide methods and apparatus for comfortably positioning a patient in an MRI or CT scanner or other imaging device (hereinafter "MRI").

It is another object of the present invention to provide methods and apparatus for comfortably positioning a patient's head or limb in an MRI.

It is a further object of the present invention to provide methods and apparatus for providing a custom fit of a patient's head or limb in an MRI.

It is another object of the present invention to provide methods and apparatus for providing optimal placement of a patient's head or limb in an MRI.

Still another object of the present invention is to provide methods and apparatus having a level of restraint that substantially diminishes or precludes all micro and macro motion of a patient's head or limb in an MRI.

Yet another object of the present invention is to provide methods and apparatus for a low cost, disposable restraining device, which will decrease the time to set up a patient for scanning, thereby further improving MRI productivity.

Yet another object is to provide a custom fit for the flex/wrap or surface coils used in some MRI imaging that comfortably secures and restrains the body part and achieves rigid, yet comfortable fixation of the coil to the patient and to the MRI.

It is another object of the present invention to provide methods and apparatus for improving the intrinsic imaging quality of the MRI due to, for example, improved field homogeneity, signal to noise ratio, fat saturation, etc.

Still another object of the present invention is to provide methods and apparatus for improving patient tolerance of the imaging procedure by improving patient comfort.

These and other objects and advantages of the invention will be better understood by reference to the detailed description or will be appreciated by the practice of the invention. Consistent with the foregoing objects, and in accordance with the embodiments as embodied and broadly described herein, the restraining apparatus of the present invention will limit motion on the macro and micro scales by providing a custom fit, while also improving patient comfort. The restraining apparatus preferably comprises a disposable component, including a castable sleeve and, in a preferred embodiment, an expandable sleeve, both of which are used to fix the patient into the coil. The castable sleeve encircles the limb of a patient, and is filled with a quickly casting material. The casting material is MRI compatible, safe and rapid setting, which will decrease the time to set up a patient for scanning, thereby further improving MRI productivity. In addition, the casting material may augment the quality of the image, such as by improving the signal to noise ratio, the field homogeneity, and the fat saturation. The resulting cast sleeve is also MRI compatible and provides a comfortable custom fit for the patient that helps restrain the patient in the imaging device.

In one preferred embodiment, the expandable sleeve encircles the castable sleeve and expands to conform to the inner dimensions of a particular MRI coil or CT scanner.

Alternatively, the apparatus includes a castable sleeve that conforms via the castable material to both the limb of the patient and the inner dimension of a particular MRI coil or CT scanner.

Alternatively, the apparatus includes a castable sleeve for casting around a flex/wrap or surface coil. In one embodiment, the surface coil is wrapped around the limb of a patient and the castable sleeve is positioned over the surface coil or the castable sleeve is integrated into the surface coil to ensure rigid fixation and custom fit of the coil between the limb and the coil, as well as the coil and the MRI scanner.

BRIEF DESCRIPTION OF THE DRAWINGS

The foregoing and other objects and features of the present embodiments will become more fully apparent from the following description and appended claims, taken in conjunction with the accompanying drawings. Understanding that these drawings depict only typical embodiments and are, therefore, not to be considered limiting of the invention's scope, the embodiments will be described with additional specificity and detail through use of the accompanying drawings in which:

DETAILED DESCRIPTION

It will be readily understood that the components of the embodiments, as generally illustrated in the Figures and described herein, could be arranged and designed in a wide variety of different configurations. Thus, the following more detailed description of the embodiments of the apparatus and methods disclosed, as represented in FIGS. 1 through 12, is not intended to limit the scope of the invention, as claimed, but is merely representative of the presently preferred embodiments.

The presently preferred embodiments will be best understood by reference to the Figures, wherein like parts are designated by like numerals throughout. While the preferred embodiments pertain to MRI and to CT scanners, and to other imaging devices, the following detailed description will focus on use with an MRI. It will be appreciated that MRI and CT scanners, and other imaging devices for use with different body parts are within the scope of the present invention. For ease of the present discussion, however, a preferred embodiment of the invention will be described with reference to a small MRI coil such as for use imaging the wrist of a patient.

Figure 1:
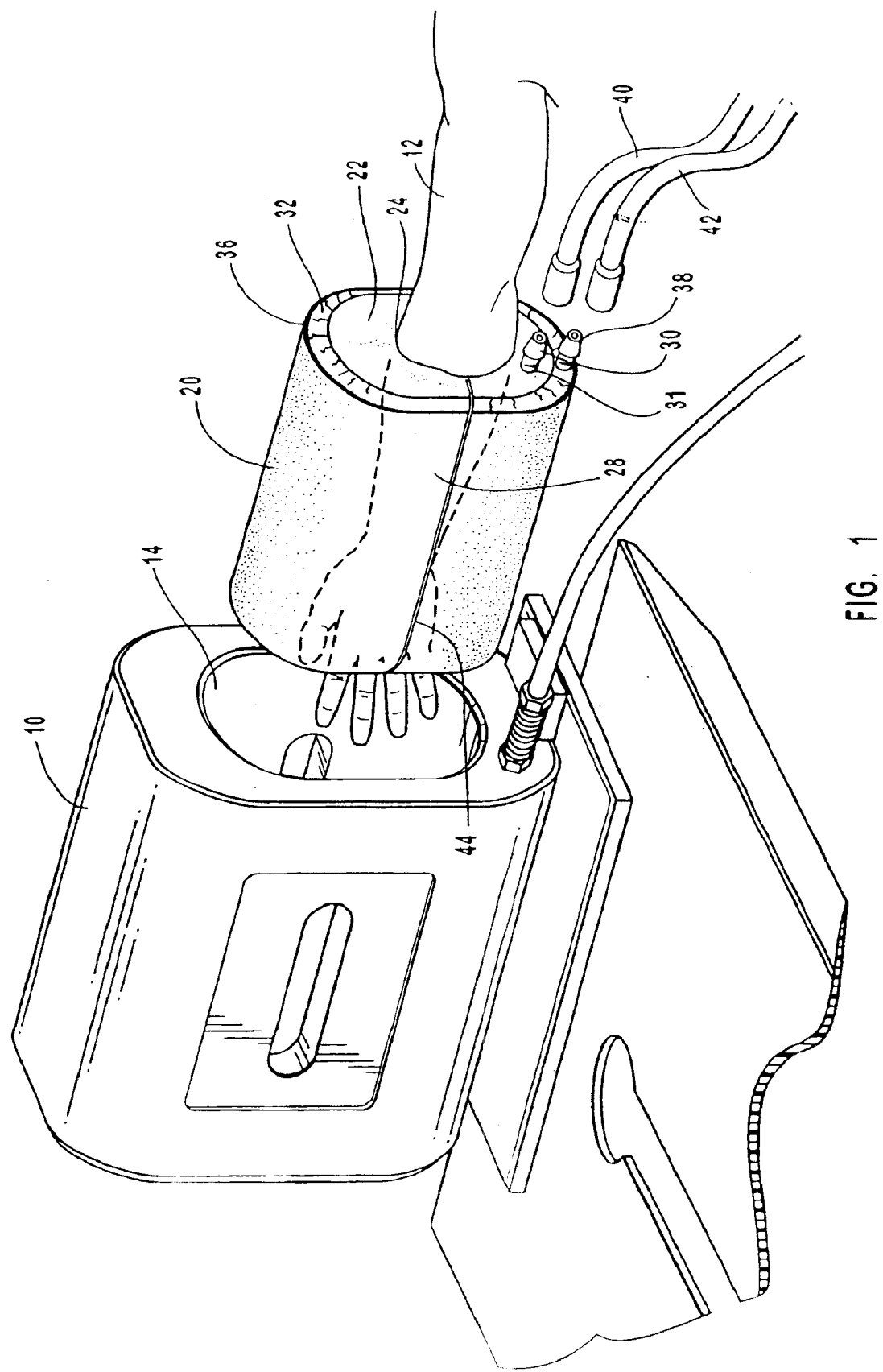
FIG. 1 is perspective view of an embodiment of an apparatus with a patient's limb fixed therein, being inserted into an MRI coil.

FIG. 1 is a visual representation of the features of the present invention that solve the problems encountered with conventional stabilizing and restraining devices. FIG. 1 depicts one presently preferred embodiment of an apparatus generally labeled 20 for stabilizing and restraining a limb of the patient in a medical apparatus. In FIG. 1 the medical device illustrated is a small MRI coil 10 such as for use on the wrist of a patient. As will be discussed further herein, the dimensions inside of the MRI coil 10 (the inner dimensions 14) correspond to the outside of apparatus 20.

The apparatus of one presently preferred embodiment includes both a castable sleeve 22 and an expandable sleeve 32. The castable sleeve preferably comprises concentric layers of plastic or other suitable fluid-impermeable material designed for comfortable contact with the patient. In one embodiment, the material provides thermal comfort, and is safe and easily removable.

Figure 3:
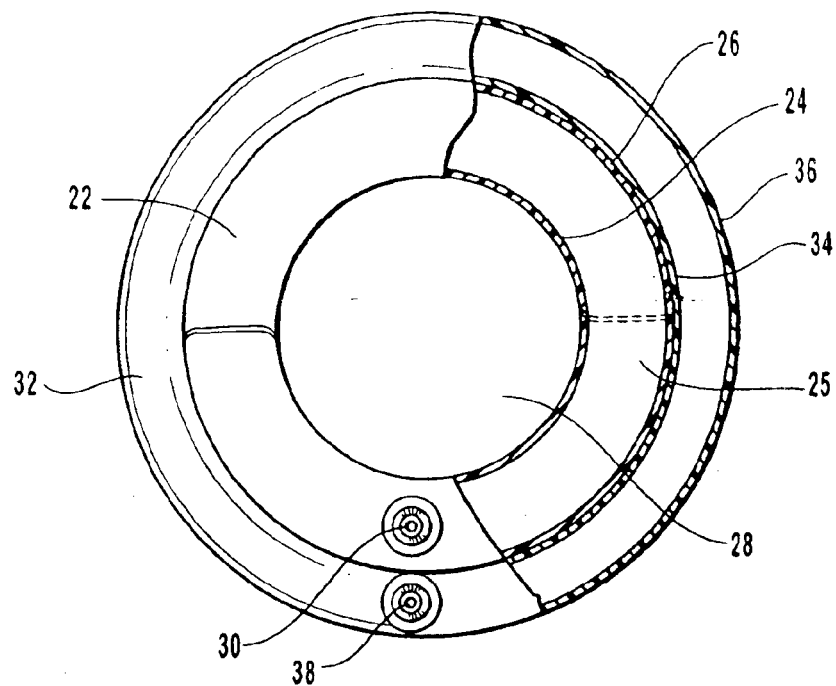
FIG. 3 is cut-away view of an end of an embodiment of the apparatus of the present invention.

As best illustrated in FIG. 3, castable sleeve 22 comprises a proximal concentric layer 24 and a distal concentric layer 26. The proximal concentric layer 24 circumscribes a void 28 through which the limb of the patient is inserted. The castable sleeve may be open at one end only to receive the limb of the patient, or alternatively, at both ends. In either embodiment, the quick cast material will expand to consume the available space and to cast the limb. Upon introduction of a quick cast material into the castable sleeve, proximal concentric layer of the castable sleeve will form a custom fit about the patient's limb, while distal concentric layer will expand only to a limited degree.

The tactile elasticity and strength of the proximal and distal layers are preferably optimized for patient comfort and for rigidity and fixation to the imaging device. For example, in a preferred embodiment, distal layer 26 comprises limited elasticity to limit expansion outward of the casting material, while proximal layer 24 comprises greater elasticity and pliability to optimize conforming to the contours of the patient.

In the inner space 25 between the concentric layers, the castable sleeve permits the introduction of quick cast material. Preferably this material comprises an expandable and castable foam. Alternatively, the material may comprise an expandable and castable gel. One of ordinary skill in the art will understand that other expandable and castable materials are within the scope of the present invention. The quick cast material preferably expands due to intrinsic expansion of the material. Alternatively, the quick cast material expands due to pressure of the injection.

Upon introduction between the concentric layers of the castable sleeve, the quick cast material forms a custom fit cast around the patient's limb, thereby securing the limb from movement at a joint, and diminishing the degrading effects of macro and micro motion to imaging as described above. The proximal concentric layer forms a custom fit due to the expansion of the quick cast material and/or due to the pressure of introduction of the casting material. The pressure is controlled for patient safety, such as with, but not limited to, a relief valve or a pressure regulated delivery system.

Figure 4:
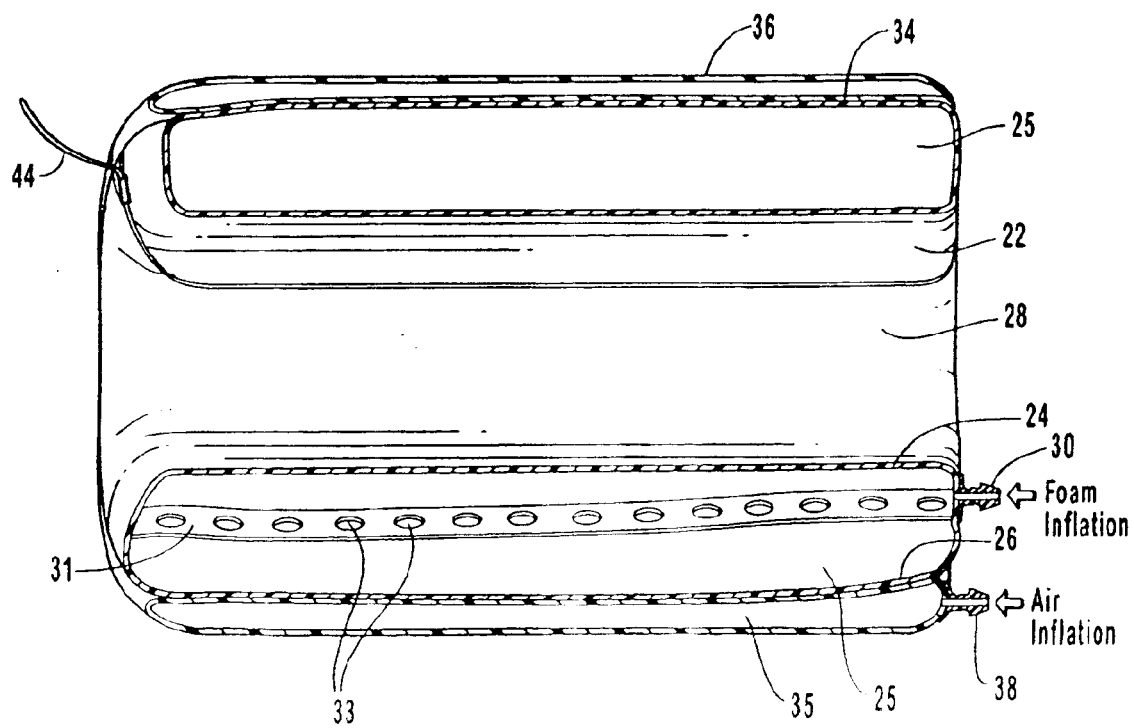
FIG. 4 is a cut-away longitudinal view of the apparatus depicted in FIG. 3.

As depicted in FIG. 1, the limb of the patient 12 is inserted into the void area 28 of the castable sleeve, the void area being defined by proximate concentric layer 24. A valve 30 is provided within the castable sleeve to provide fluid communication with the castable sleeve and a quick cast material. Upon introduction of a patient's limb into the void formed by the castable sleeve, the quick cast material is introduced through connective tubing 40 connected to valve 30. In a preferred embodiment, inner tubing 31 is connected to valve 30. Inner tubing 31 preferable extends in the inner space 25 between proximal 24 and distal 26 concentric layers and includes a plurality of dispersion holes 33 that permit the quick cast material to be introduced quickly and optimally dispersed along the entire length of the limb in the castable sleeve, as illustrated in FIG. 4.

Figure 6:
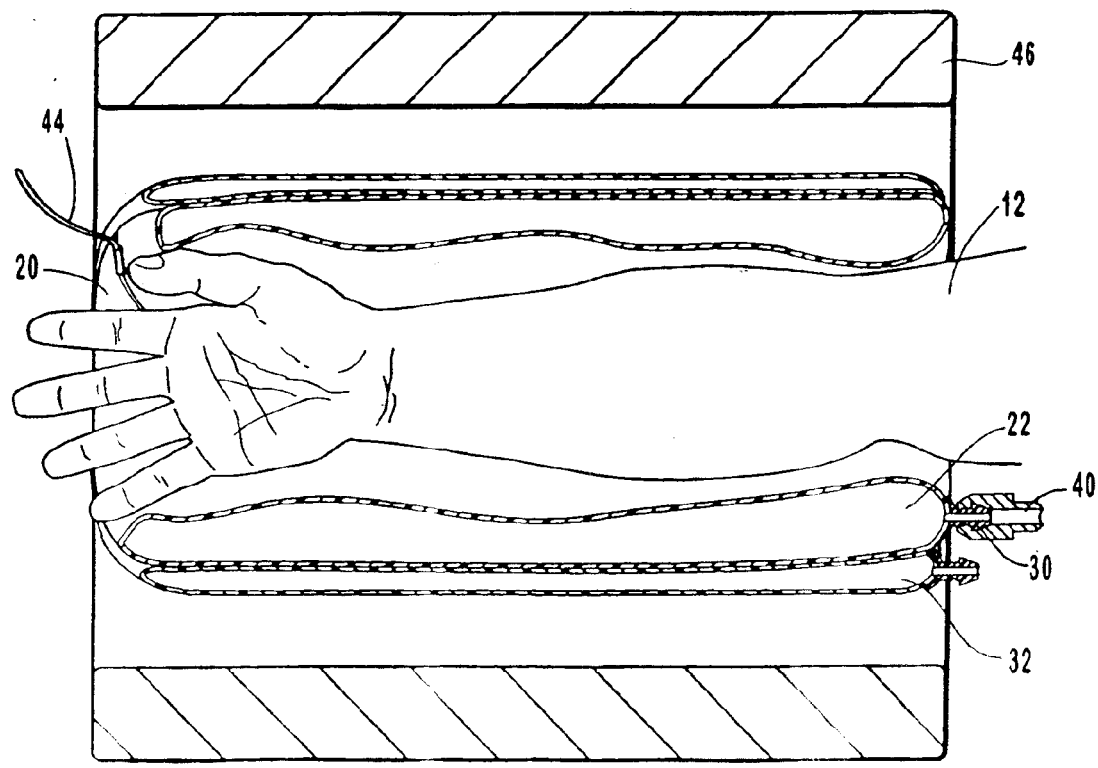
FIG. 6 illustrates a cross section of an embodiment of the apparatus of the present invention positioned within a mock coil.

Alternatively, tubing 31 may just extend slightly into the castable sleeve for introduction of the quick cast material therein, as illustrated in FIG. 1. Alternatively, valve 30 may open into the castable sleeve for introduction of the quick cast material therein, without tubing 31, as illustrated in FIG. 6. In an alternate embodiment, a plurality of valves and or tubes for introduction of the quick cast material are provided along the castable sleeve.

An expandable sleeve 32 is also provided in the apparatus illustrated in FIG. 1. The expandable sleeve preferably comprises concentric layers of plastic or other suitable fluid-impermeable material. Between the concentric layers, the expandable sleeve permits the introduction of a material capable of expanding and/or inflating the expandable sleeve. Preferably this material comprises air. One of skill in the art will recognize that other materials that will expand and/or inflate the expandable sleeve are within the scope of the present invention. While in no way limiting the scope of the present invention, the term "inflation" will be used herein after to describe the expansion of the expandable sleeve.

The expandable sleeve preferably surrounds the castable sleeve and is attached thereto. The expandable and castable sleeves are permanently attached to one another, or alternatively are removably attached, such as with hook and loop fasteners, straps, and the like. In an alternate embodiment, the expandable sleeve contacts the castable sleeve but is not attached thereto. For example, the expandable sleeve is attached to the MRI coil such that upon insertion of a cast sleeve into the coil, the expandable sleeve is inflated to hold the cast sleeve in place.

In the embodiment of the invention illustrated in FIG. 3, the distal concentric layer 26 of the castable sleeve is attached to the expandable sleeve 32 of the apparatus 20. Similar to the castable sleeve, the expandable sleeve includes concentric layers: an inner layer 34 and an outer layer 36. The inner layer 34 contacts the distal concentric layer 26 of the castable sleeve 22. The outer layer 36 contacts the inner dimensions of a coil. Preferably, upon inflation of the expandable sleeve 32, the outer layer 36 of the expandable sleeve 32 will precisely correspond to the inner dimensions of an MRI coil such that the apparatus is fixed within the MRI coil.

The tactile elasticity and strength of the inner and outer layers are preferably optimized for patient comfort and for rigidity and fixation to the imaging device. For example, in a preferred embodiment, inner layer 34 comprises limited elasticity to limit expansion outward toward the castable sleeve, while outer layer 36 comprises greater elasticity and pliability to optimize conforming to the contours of the imaging device.

Turning to FIG. 1, the expandable sleeve 32 is preferably inflated via valve 38 with air through connective tubing 42, which will be attached thereto for inflation and deflation of the expandable sleeve. Alternatively, as noted above, one of skill in the art will recognize that other materials that provide ease of inflation and deflation are within the scope of the present invention.

The expandable sleeve is preferably inflated upon introduction of the patient's limb (already cast in the castable sleeve) into the MRI coil. The expandable sleeve is inflated to fill all available space and thereby conform precisely to the inner dimensions of the coil. Once the expandable sleeve is inflated with the cast limb in the castable sleeve, it stabilizes the limb from both micro and macro movement within the MRI coil.

Figure 10:
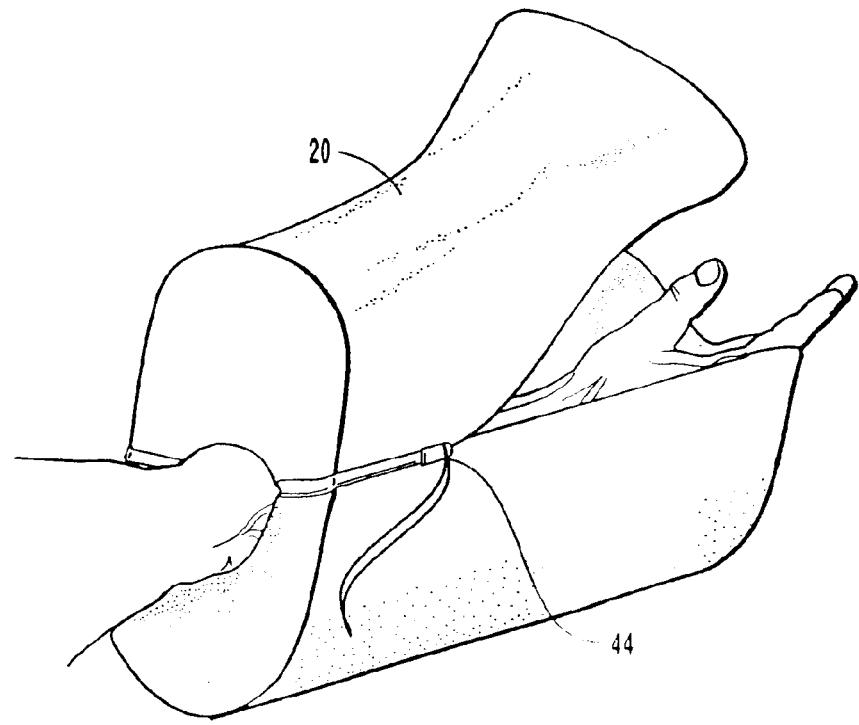
FIG. 10 illustrates an embodiment of the apparatus of the present invention after the completion of use of the apparatus with the rip cord tearing apart the apparatus for removal from the patient's limb.

Upon completion of the imaging procedure, the expandable sleeve is easily evacuated by releasing the connective tubing 42 from the valve 38. Alternatively, a vacuum is pulled through the connective tubing to evacuate the air. In one embodiment, the apparatus of the present invention is removed from the limb of a patient via at least one rip cord 44, as illustrated in FIG. 10. The rip cord 44 tears along the quick cast material in the castable sleeve, thereby aiding in removal of the apparatus from the limb of the patient. Alternatively, scissors or other implements are used to aid in removal of the castable sleeve. Alternatively, a substance that breaks down the quick cast material is introduced into the castable sleeve to aid in removal thereof.

In an alternate embodiment, the apparatus comprises a castable sleeve. In this embodiment, the limb of the patient is inserted into the castable sleeve, which is then inserted into the MRI coil. The quick cast material, which expands due to pressure of injection or due to intrinsic expansion of the material, is then introduced into the castable sleeve, thereby casting the limb and conforming to the inner dimensions of the MRI coil, without the need for the expandable sleeve. A substance that breaks down the quick cast material can be injected into the castable sleeve upon completion of imaging for removal of the limb from the coil. Alternatively, as described above, scissors, a rip cord, or other implement are used to remove the castable sleeve. In such an embodiment, the MRI coil preferably includes a clam shell opening for removal of the cast sleeve from the coil.

Figure 2:
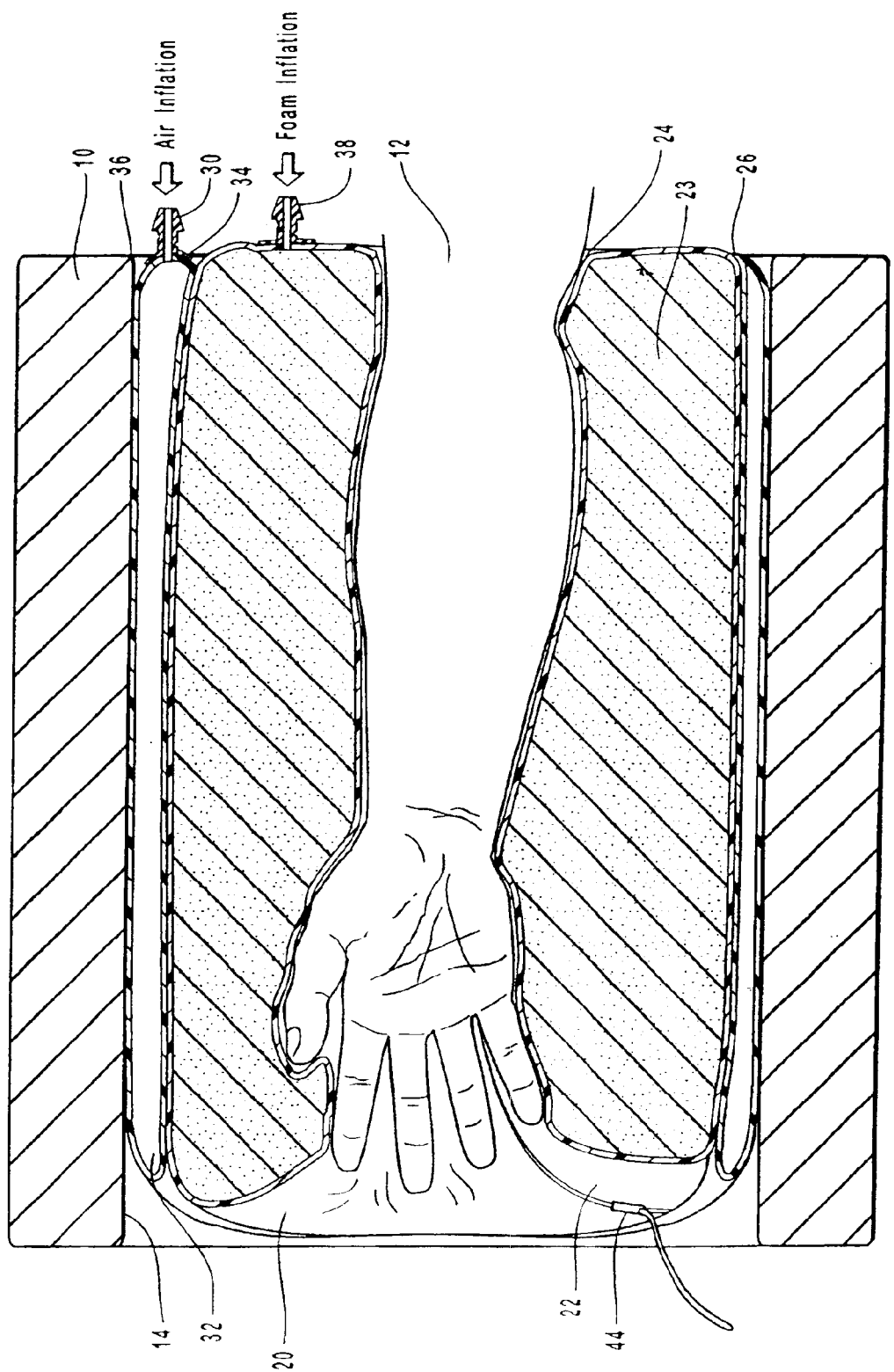
FIG. 2 is a cross-sectional view of an embodiment of an apparatus with a patient's limb fixed therein, and further fixed within an MRI coil.

Turning to FIG. 2, there is illustrated a cross section of an embodiment of the apparatus and the patient's limb 12 including the castable sleeve 20 cast thereon, which have been inserted into MRI coil 10. One will note that the expandable sleeve 32 has been sufficiently inflated to correspond to the inner dimensions 14 of the MRI coil 10 such that a tight fit has been accomplished. In addition, castable sleeve 22 has been expanded with quick cast material such that the patient's wrist is restrained from micro and macro motion within the MRI coil.

FIG. 4 is yet another illustration of a preferred embodiment of the present invention with portions cut away to illustrate the castable and expandable sleeves and the void areas in the apparatus. In particular, FIG. 4 illustrates the inner space 25 of castable sleeve 22 for introduction of the quick cast material. FIG. 4 also illustrates the inflatable space 35 in expandable sleeve that inflates to conform to the inner dimensions of an MRI coil.

Figure 5:
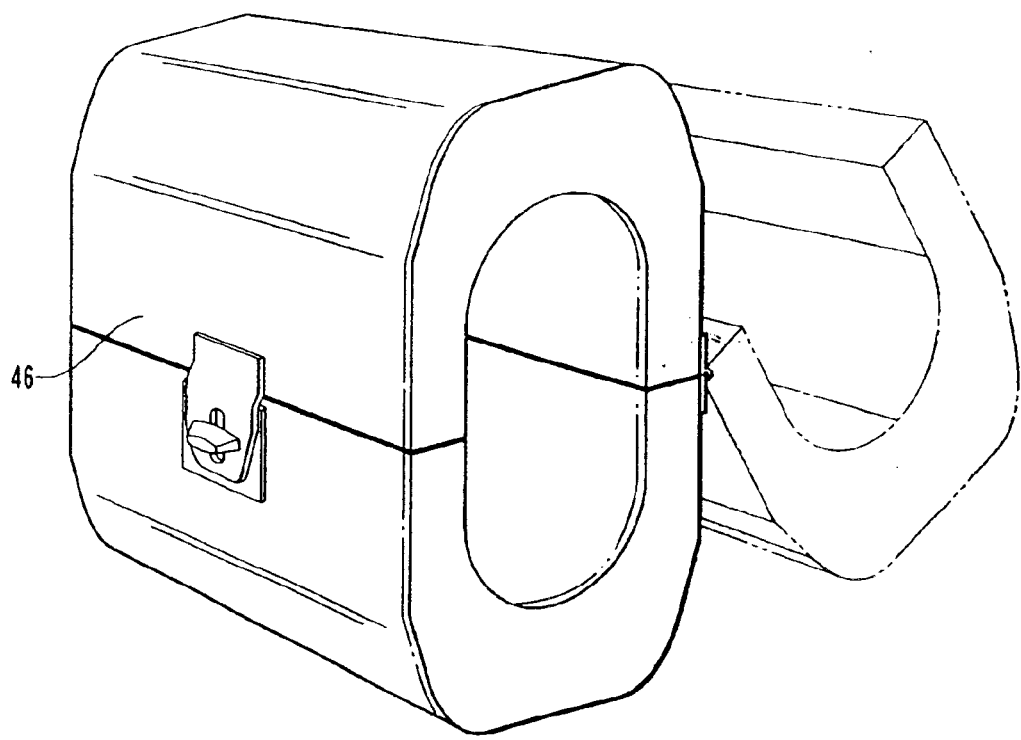
FIG. 5 is a perspective view of a mock coil in accordance with an embodiment of the present invention.

FIG. 5 illustrates a mock coil 46 that emulates an actual MRI coil. Such a mock coil is used for pre-molding the apparatus of the present invention to accommodate a particular MRI coil. This mock coil 46 will save valuable MRI coil time by enabling the user to properly mold and configure an apparatus according to the present invention to conform to the actual inner dimensions of an MRI coil without actually using the MRI coil time to do so. Preferably, a mock coil is configured to correspond internally to the internal dimension of an actual MRI coil. Alternatively, the inner dimensions of the mock coil are slightly smaller than the inner dimensions of the actual coil to allow for void space in the actual coil. The void space is then filled by the expandable sleeve upon inflation thereof. It will be appreciated that numerous such mock coils would be available to the imaging practitioner to correspond to the actual MRI coils needed for patient tests. Further, such mock coils are preferably formed from light weight materials to promote ease of handling.

In one preferred method of the present invention, a patient's limb is inserted into the void space of the castable sleeve such that the proximal layer is in contact with the patient's limb. A quick cast material is then inserted into the inner space between the proximal and distal layers. The quick cast material conforms to and casts the patient's limb. The cast limb is then inserted into an MRI coil. The expandable sleeve is inflated to conform to the inner dimensions of the coil and to restrain and secure the patient's limb therein. The patient and coil may then be positioned within the MRI scanner for imaging.

Upon completion of the imaging, the patient and coil are removed from the MRI scanner. The expandable sleeve of the apparatus is deflated and the apparatus still cast about the limb are removed from the coil. The rip cord is then torn along the length of the apparatus to tear apart the cast material such that limb can be removed from the apparatus. Alternatively, the apparatus is cut from the limb. Alternatively, a substance that breaks down the quick cast material is inserted into the castable sleeve.

Turning the figures to illustrate a method incorporating a mock coil, FIG. 6 illustrates the limb 12 of a patient inserted into apparatus 20. Castable sleeve 22 is not yet expanded to cast the limb or conform to the inner dimensions of the mock coil 46, and expandable sleeve 32 is not yet inflated to conform to the inner dimensions of the actual coil (not pictured).

Figure 7:
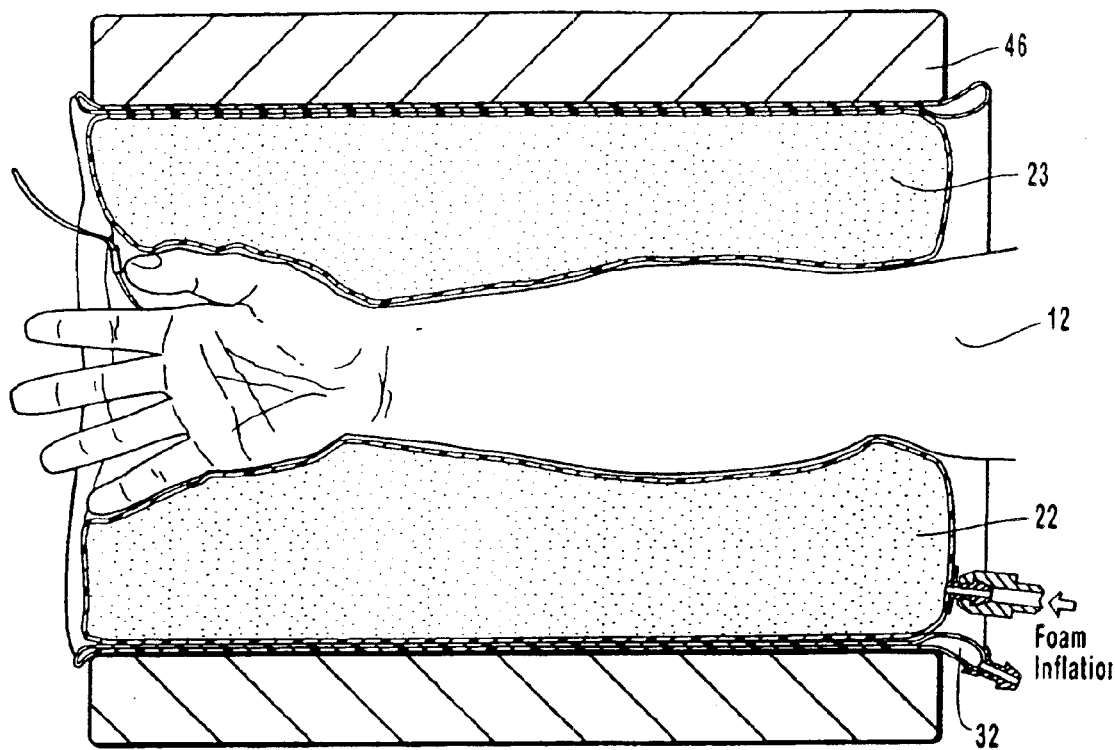
FIG. 7 illustrates the apparatus of FIG. 6 with the castable material casting the limb of a patient, and conforming to the inner dimension of the mock coil.

FIG. 7 illustrates the limb 12 of the patient within the apparatus of the present invention wherein the quick cast material 23 has been introduced into the castable sleeve 22 and has conformed to the limb of the patient thereby casting the limb of the patient. In addition, the quick cast material has expanded to substantially fill the volume of space inside of the mock coil 46.

Figure 8:
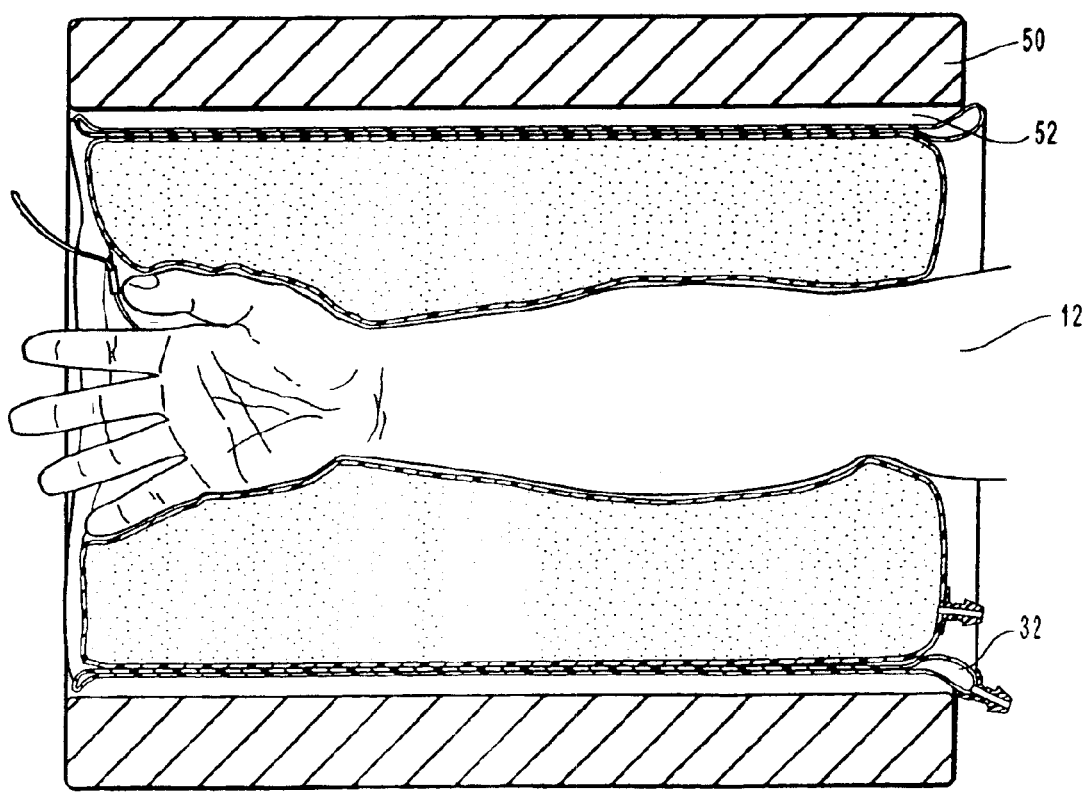
FIG. 8 illustrates the apparatus of FIG. 6 with the castable material casting the limb of a patient and leaving a void between the inner dimension of the actual MRI coil and the expandable sleeve of the apparatus.
Figure 9:
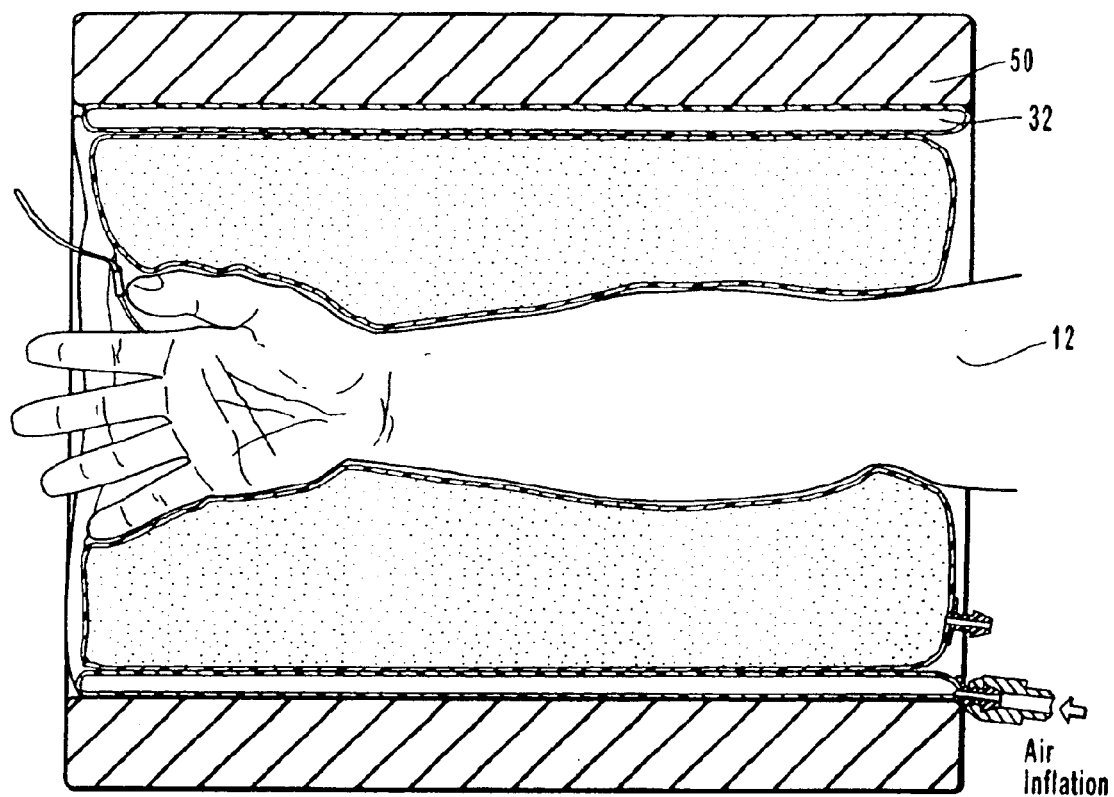
FIG. 9 illustrates the apparatus of FIG. 8 with the expandable sleeve inflated so as to conform to the inner dimensions of the MRI coil.

In FIG. 8, the cast limb from FIG. 7 has been inserted into an actual MRI coil 50. The expansion of the castable sleeve has significantly filled the inner volume of the coil. The volume 52 left in the inside of the coil 50 between the expandable sleeve 32 and the coil will require inflation of the expandable sleeve. FIG. 9 illustrates such inflation. In this figure, the expandable sleeve 32 has been inflated to conform to the inner dimensions of the coil. The limb 12 is thereby prevented from micro and macro movement within the coil.

Turning to FIG. 10, apparatus 20 is illustrated after having been removed from the MRI coil upon completion of a scan. Further, the rip cord 44 is illustrated being used to tear apart the apparatus to release it from patient's limb.

As an alternative to the standard coils described above, imaging practitioners utilize surface coils, which are positioned around the limb or portion of the body of a patient. Such a coil is flexible and wraps around the limb or portion of the body thereby placing the coil directly on the surface or skin of the patient. The surface coil, as will be appreciated by those of skill in the art, provides improved imaging from standard coils described above. This improved imaging derives from the improved signal to noise ratio by placing the coil as close as possible to the limb or portion of the body being imaged, thereby diminishing dead space that can interfere with the image. Yet, the surface coil still suffers from motion degradation. Existing surface coils have no fixation system, thus both macro and micro motion negatively affect the imaging.

Thus, in an alternate embodiment, a castable sleeve is used as a cast to surround the surface coil and cause the surface coil to conform to the limb of the patient, thereby diminishing image degradation via micro motion. The limb with the surface coil cast to it is then secured in the MRI scanner with a clamp or other fixation means, thereby diminishing image degradation via macro motion. Thus, the advantage of the surface coil is combined with rigid immobilization and perfect positioning within the MRI scanner.

Figure 12:
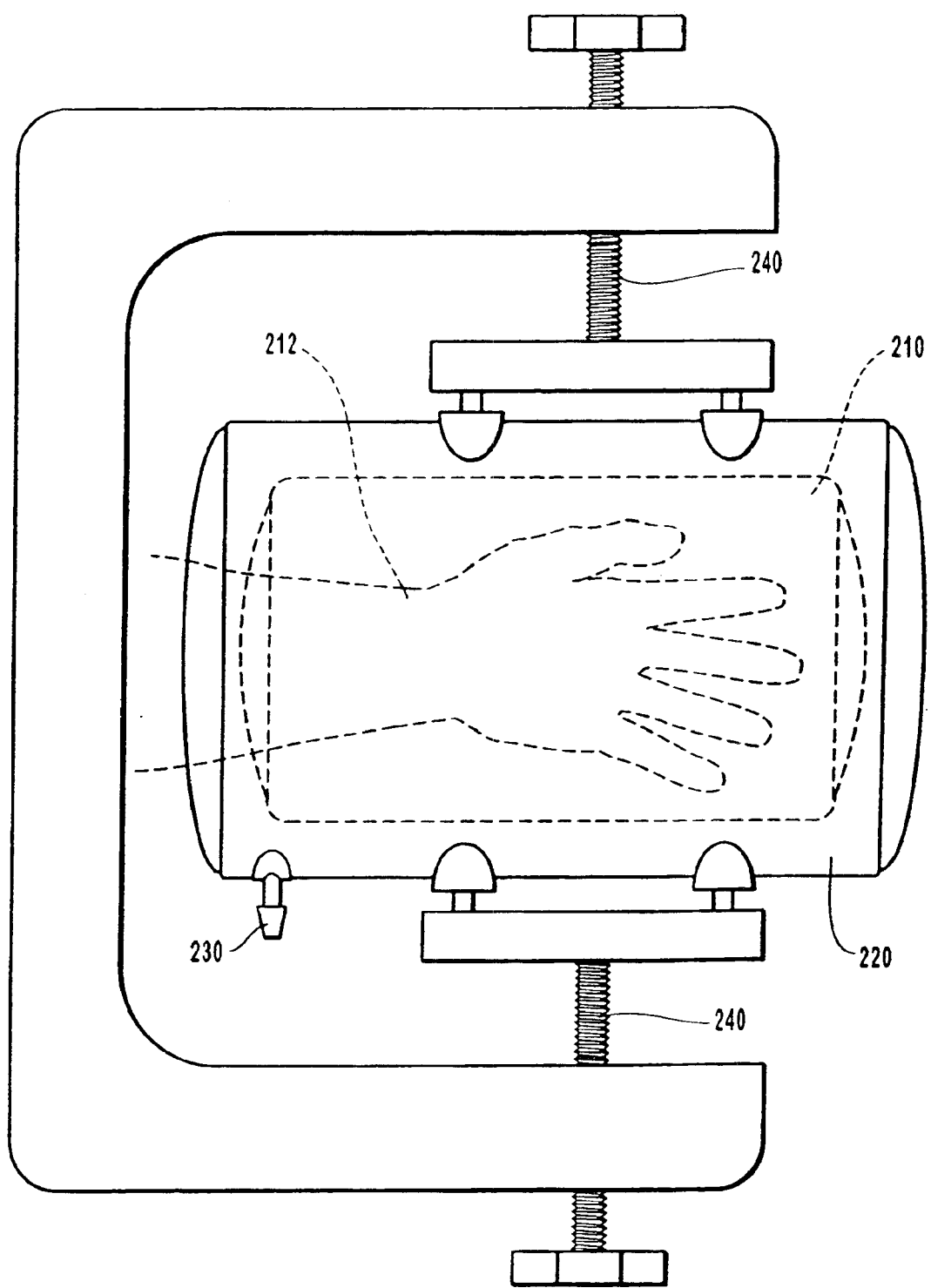
FIG. 12 is an illustration of an alternate embodiment of the present invention comprising a castable sleeve cast about a surface coil, and fixed into and MRI scanner via clamps.

In the embodiment depicted in FIG. 12, patient limb 212 is surrounded by surface coil 210, which is surrounded by castable sleeve 220. In one embodiment, the castable sleeve is unattached to the surface coil. In an alternate embodiment, the castable sleeve is removably attached to the surface coil. In yet another alternate embodiment, the castable sleeve is integrated with the surface coil.

The castable sleeve 220 includes valve 230 for introduction of quick cast material into castable sleeve as described above with respect to a standard coil. Upon expansion of the quick cast material, the surface coil is fixed in place snuggly about the patient's limb, thereby substantially diminishing any micro motion. The castable sleeve is then secured vis-a-vis the MRI magnet, thereby substantially precluding the castable sleeve, surface coil, and limb from gross motion. In FIG. 12, clamps 240 secure the casted flex coil in place in the magnet. The clamps are preferably adjustable for height and lateral positioning of the limb within the MRI scanner, which thereby optimizes imaging and patient comfort. One of skill in the art will appreciate that other means for securing the cast surface coil and limb in place include, but are not limited to, straps and the like.

Turning to the method for casting and restraining a surface coil in and MRI scanner, a surface coil is wrapped about the limb of a patient. The castable sleeve is positioned about the surface coil. The quick cast material is then introduced into the castable sleeve, thereby casting the surface coil in place about the limb. The limb with the coil cast thereon is then secured in the MRI scanner such as with clamps as described above. The clamps are then adjusted so that the limb is precisely positioned within the MRI scanner for optimum imaging.

Figure 11:
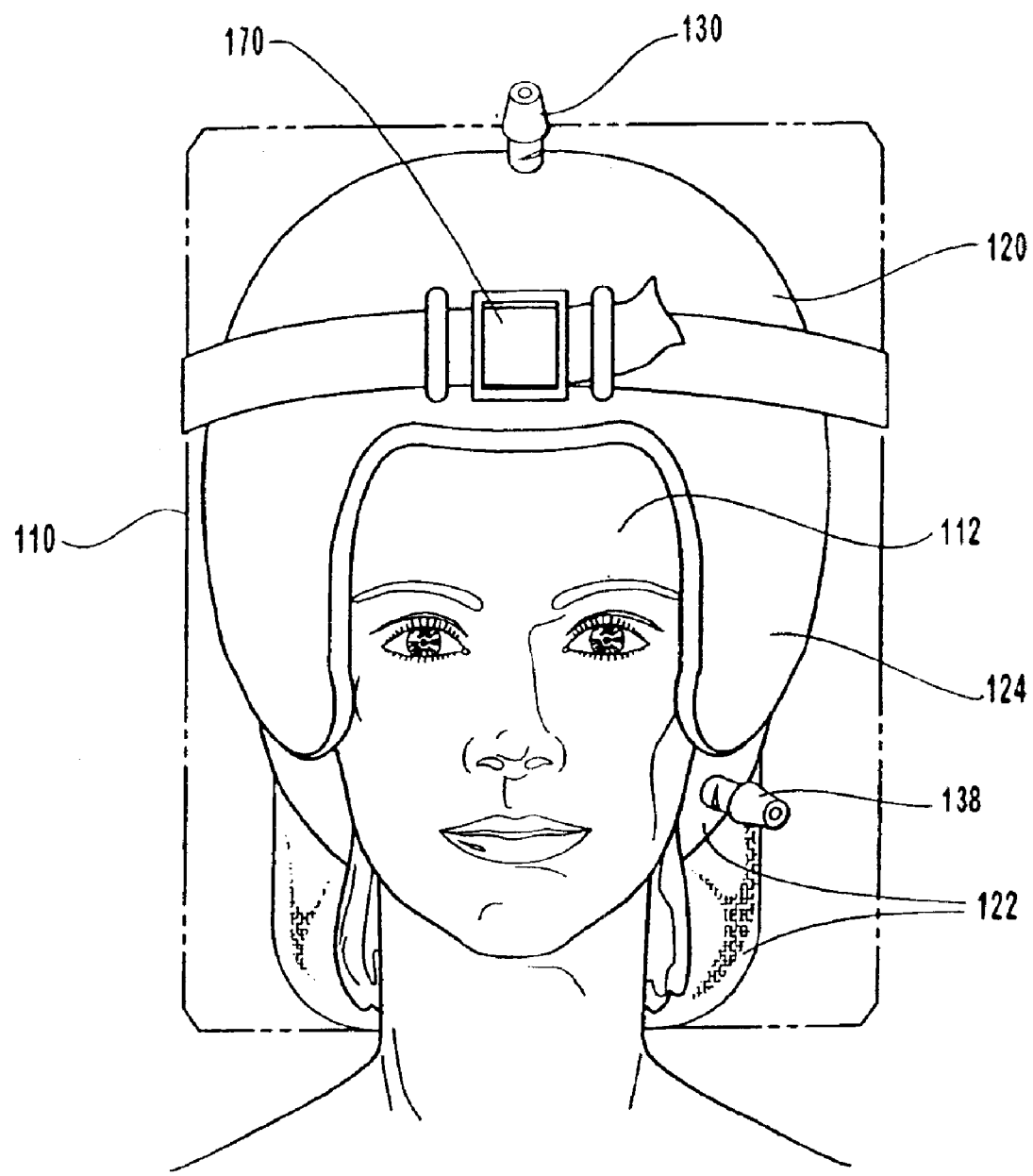
FIG. 11 is an illustration of an alternate embodiment of the present invention comprising an apparatus for securing the head of a patient in an MRI or CT scan or other imaging device.

In an alternate embodiment depicted in FIG. 11, an apparatus is provided for a head MRI or CT scan. The head apparatus 120 includes castable chambers 122 and expandable chamber 124. The apparatus surrounds the patient's head 112 without obstruction of the patient's airway, eyesight, or vessels. As illustrated in FIG. 11, belt 170 secures the head to the MRI coil 110. Valve 130 permits introduction of an expandable material such as air to inflate expandable chamber 124. Valve 138 permits introduction of a quick cast material into castable chambers.

In an alternate embodiment of any of the aforementioned embodiments, the castable sleeve or chamber, and/or the expandable sleeve or chamber, may include a plurality of sub-chambers therewithin. Such subchambers may form a plurality of fluidly interconnected individual pillow-like expansions, expandable via introduction of castable or expandable material through at least one valve. Alternatively, each of the plurality of subchambers may have its own valve for introduction of expandable or castable material.

As will be appreciated by those skilled in the art, there are a variety of means to implement the present embodiments to various configurations of MRI and CT scanners. Further, it is understood that the above description is not meant to limit the scope of the present invention.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed is:

1. An apparatus for stabilizing and restraining a limb of a patient in an imaging device, the apparatus comprising:
   (a) a castable sleeve, the castable sleeve including a proximal layer and a distal layer, the proximal layer contacting at least a portion of the patient's limb; and
   (b) an expandable sleeve surrounding the distal layer of the castable sleeve;
   wherein the castable sleeve has an inner space between the proximal and distal layers, the inner space being capable of receiving a quick cast material;
   wherein the castable sleeve includes at least one valve for introduction of the quick cast material; and
   wherein inner tubing is connected to the at least one valve and includes dispersion holes that permit the quick cast material to be optimally dispersed throughout the castable sleeve.

2. An apparatus for stabilizing and restraining a patient in an imaging device, the apparatus comprising:
   (a) a castable sleeve, expandable sleeve, at least one valve and inner tubing;
   (b) the expandable sleeve surrounding and attached to the castable sleeve;
   (c) the castable sleeve including a proximal layer and a distal layer, the proximal layer contacting at least a portion of the patient's body, wherein the castable sleeve has an inner space between the proximal and distal layers, the inner space in fluid communication with a quick cast material;
   (d) the at least one valve with one end of at least one of the at least one valves in the inner space; and
   (e) the inner tubing is connected to the at least one valve and includes dispersion holes that permit the quick cast material to be optimally dispersed throughout the castable sleeve.

3. An apparatus in accordance with claim 2, wherein the castable sleeve forms a cast around a surface coil, the surface coil having first been wrapped around the portion of the patient's body.

4. An apparatus in accordance with claim 2, wherein the distal layer comprises means for securing the apparatus to an MRI scanner.

5. An apparatus in accordance with claim 2, wherein the imaging device is an MRI coil.

6. An apparatus in accordance with claim 2, wherein the imaging device is a mock coil.

* * * * *